US009138504B2

(12) United States Patent
Li et al.

(10) Patent No.: US 9,138,504 B2

(45) Date of Patent: Sep. 22, 2015

(54) PLASMA DRIVEN CATALYST SYSTEM FOR DISINFECTION AND PURIFICATION OF GASES

(71) Applicant: Nano and Advanced Materials Institute Limited, Hong Kong (HK)

(72) Inventors: Jifan Li, Hong Kong (HK); Wai Man Peter Lee, Hong Kong (HK); Wing Kei Ho, Hong Kong (HK)

(73) Assignee: NANO AND ADVANCED MATERIALS INSTITUTE LIMITED, Hong Kong (HK)

(*) Notice: Subject to any disclaimer, the term of this patent is extended or adjusted under 35 U.S.C. 154(b) by 0 days.

(21) Appl. No.: 14/446,311

(22) Filed: Jul. 29, 2014

(65) Prior Publication Data

US 2015/0050191 A1 Feb. 19, 2015

Related U.S. Application Data

(60) Provisional application No. 61/959,252, filed on Aug. 19, 2013.

(51) Int. Cl.

*A61L 9/00* (2006.01)
*A61L 9/03* (2006.01)

(Continued)

(52) U.S. Cl.

CPC . *A61L 9/22* (2013.01); *A61L 9/205* (2013.01); *A61L 2209/14* (2013.01)

(58) Field of Classification Search

CPC .............. A61L 9/00; A61L 9/03; A61L 9/205
USPC .............. 422/121, 123, 305–306; 96/15, 223, 96/186.04

See application file for complete search history.

(56) References Cited

U.S. PATENT DOCUMENTS

| | | | |
|---|---|---|---|
| 8,475,723 B2 | 7/2013 | Keras | |
| 2003/0136661 A1 | 7/2003 | Kong et al. | |
| 2009/0178915 A1* | 7/2009 | Otaka et al. | 204/164 |

(Continued)

FOREIGN PATENT DOCUMENTS

| | | |
|---|---|---|
| CN | 1919425 A | 2/2007 |
| CN | 2869653 Y | 2/2007 |

(Continued)

OTHER PUBLICATIONS

T. Ochiai et al., "An effective method for a separation of smoking area by using novel photocatalysis-plasma synergistic air-cleaner," Chemical Engineering Journal, vol. 209, pp. 313-317, 2012.

(Continued)

*Primary Examiner* — Monzer R Chorbaji

(74) *Attorney, Agent, or Firm* — Ella Cheong Hong Kong; Sam T. Yip

(57) ABSTRACT

The present invention relates to a novel plasma driven catalyst apparatus for disinfecting and purifying air. The apparatus has a synergistically favorable effect from plasma and catalyst on high disinfecting and purifying efficiency and efficacy, low by-product formation, and low energy consumption. The plasma combined with catalyst enhances the production of new active species, increases the oxidizing power of the plasma discharge, as well as activate the catalyst that additionally contributes towards the disinfection and purification process and the elimination of toxic by-products.

20 Claims, 4 Drawing Sheets

(51) Int. Cl.

| | |
|---|---|
| ***A61L 9/22*** | (2006.01) |
| ***A61L 9/20*** | (2006.01) |

(56) References Cited

U.S. PATENT DOCUMENTS

| | | | |
|---|---|---|---|
| 2010/0134947 | A1 | 6/2010 | Goudy, Jr. |
| 2011/0180149 | A1 | 7/2011 | Fine et al. |

FOREIGN PATENT DOCUMENTS

| | | | |
|---|---|---|---|
| CN | 201290918 | Y | 8/2009 |
| CN | 101799203 | B | 4/2014 |
| EP | 1671659 | A1 | 6/2006 |
| EP | 1782841 | A1 | 5/2007 |
| WO | 9103315 | A1 | 3/1991 |
| WO | 2007093810 | A2 | 8/2007 |

OTHER PUBLICATIONS

R. B. Sun et al., "Decomposition of low-concentration gas-phase toluene using plasma-driven photocatalyst reactor," Atmospheric Environment, vol. 41, 32, 6853-6859, 2007.

J. V. Durme et al., "Efficient toluene abatement in indoor air by a plasma catalytic hybrid system," Applied Catalysis B: Environmental, vol. 74, 1-2, 161-169, 2007.

A. G. Bubnov et al., "Plasma-Catalytic Decomposition of Phenols in Atmospheric Pressure Dielectric Barrier Discharge," vol. 26, 1, 19-30, 2006.

* cited by examiner

PLASMA DRIVEN CATALYST SYSTEM FOR DISINFECTION AND PURIFICATION OF GASES

CROSS REFERENCE TO RELATED APPLICATION

Pursuant to 35 U.S.C. §119(e), this is a non-provisional patent application which claims benefit from U.S. provisional patent application Ser. No. 61/959,252 filed Aug. 19, 2013, and the disclosure of which is incorporated herein by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the use of plasma driven catalyst (PDC) technology for disinfecting, cleaning and purifying air. More particularly, the present invention provides air purification apparatuses and systems with plasma driven catalyst technology for indoor air quality improvement in domestic and industrial environment.

BACKGROUND

According to various researches, there is about 80% of the time in a day that urban population spends in an indoor environment, such as homes, offices, cinemas, restaurants, stores, and other semi-enclosed spaces. The air quality in these semi-enclosed spaces may be poor due to a variety of indoor air pollutant sources such as smoking, cooking fumes, wallpaper glue, coils, burning oil heaters, smog, PM2.5, etc. Continuous or intermittent discharge of various pollutants can cause severe human health damage and even death. Maintaining appropriate indoor air quality by ventilation often draws outdoor air to dilute indoor air space. However, if the outdoor air quality is poor or there is a lack of capacity for indoor ventilation, indoor air pollution continues. Thus, an air purification system is needed to purify the indoor air so as to improve the air quality.

Plasma is known to be a gas with ionized molecules, which contains a number of components like electrons of different energy, positive and negative ions, and neutral particles. Many studies have shown that plasma is attractive for removal of NOx, SOx, odors and VOCs. Among various types of plasma, non-thermal plasma has been demonstrated as a quite effective technology to decompose VOCs and other air pollutants. The non-thermal plasma has some unique properties such as quick response at ambient temperature and under atmospheric pressure, achievement of high electron energies within short residence times, and easy operations. Besides, the plasma discharge works like an electrostatic precipitator and can be used for dust and liquid droplet collection. There is, however, a consensus among researchers that application of plasma for VOC abatement suffers from 3 main weaknesses, i.e. incomplete oxidation with emission of harmful compounds (CO, NOx, other VOCs), a poor energy efficiency, and a low mineralization degree. The incomplete oxidation leads to the formation of toxic by-products such as carbon monoxide (CO), ozone and aerosol particles, which even increase the total gaseous toxicity. Thus, these by-products formation requires the additional post-treatment system, which increases the cost and complexity of the whole air purifying system.

EP1671659 discloses a disinfecting and purifying apparatus comprising: a casing; an orientation air deflector, disposed on said casing; a movable air deflector, included in said casing and disposed at a position corresponding to said orientation air deflector; a plasma reactor, installed below said movable air deflector, and said plasma reactor installs an anion anode plate, an anion cathode plate, a plasma anode plate and a plasma cathode plate sequentially from top to bottom, and said anion anode plate, anion cathode plate, plasma anode plate and plasma cathode plate are meshed stainless steel plates, and a thin film of nano catalyst is coated on the surface of said meshed stainless steel plate. Nevertheless, using such method to generate plasma is not effective in providing a plasma with high intensity due to the catalyst coating on the anode and cathode plates.

According to a conventional air purification apparatus with the combination of plasma and catalyst for air treatment. Plasma is generated within a chamber, and a photocatalyst layer is place at the air outlet of the chamber, or at the air inlet of the chamber. Nevertheless, such configuration is not effective in air purification since the photocatalyst layer generates high air resistance toward the air purification system, leading to the attenuation of air circulation rate and the increase of the electrical burden towards fans. What's more, an additional UV light lamp is required to irradiate the photocatalyst layer for free radical generation that increases the cost and the complexity of the air purification system. Also simply applying UV irradiation may not be strong enough to generate sufficient free radicals to decompose air pollutants, ultimately causing ineffective air purification.

Consequently, there is an unmet need to have an air purification apparatus, which is effective in air pollutant removal with low air resistance, system complexity, and power consumption.

SUMMARY OF THE INVENTION

The present invention provides a plasma driven catalyst disinfecting and purifying apparatus to remove the air pollutants and improve indoor air quality. This apparatus comprises of a pre-filter, an electric fan, and a plasma reactor with catalyst inside. The plasma technology used in the present invention is based on dielectric barrier discharge (DBD) plasma. Its non-equilibrium discharge can be handily operated at atmospheric pressure conditions. DBD is formed between two parallel electrodes separated by an insulating dielectric barrier. The most important characteristic of barrier discharges is that non-equilibrium plasma conditions which is much simpler comparing with other alternative plasma technologies like electron beam, low pressure discharges, and pulsed high pressure corona discharges. This technology is easily scaled up from laboratory conditions to large industrial scale installations. The DBD plasma process uses a high voltage alternating current (AC) ranging from 4 kV to 30 kV with the frequency ranging from several hundred hertz (Hz) to few hundred kilo hertz (kHz). This sufficiently high voltage is used to ionize the media in the gap between the two electrodes, which contains a number of components like electrons of different energy, positive and negative ions, and neutral particles. These ionized components can deeply degrade the VOCs and other air pollutants into non-harmful products like $CO_2$ and $H_2O$.

However DBD plasam generates ozone and other toxic by-products during the disinfection and purificatoin process. Thus a catalyst is incorporated in the plasma reactor to remove those toxic by-products. The catalyst used in this invention is titanium dioxide ($TiO_2$) based catalyst. This $TiO_2$-based coating has a plurality of mesoporous structures with a pore size of 2-20 nm so the total effective surface area is greatly increased. The $TiO_2$ catalyst may be doped with other elements, such as Ti, Zn, Cu, Mn, La, Mo, W, V, Se, Ba, Ce, Sn, Fe, Mg, Au, Pt, Co, Ni, or Pd, or its oxides, or its alloys to enhance its photocatalytic performance. This $TiO_2$ based catalyst can be activated in the plasma reactor without additional UV light irradiation. The generated ozone and other byproducts from the DBD plasma can be eliminated by the $TiO_2$ based catalyst. The position of the catalyst can be located on the surface of the electrodes, between electrodes, or at the back end of the plasma reactor.

Accordingly, a first aspect of the presently claimed invention is to provide a plasma reactor for purifying air.

According to an embodiment of the presently claimed invention, a plasma reactor for purifying air comprises: at least two spaced plasma electrodes for generating plasma within a plasma zone between the at least two spaced plasma electrodes by an alternating current voltage; at least one insulating dielectric layer; at least one photocatalyst layer; and at least one air inlet and at least one air outlet for allowing air passing through the plasma; wherein the insulating dielectric layer is formed on at least one of the spaced plasma electrodes; wherein the photocatalyst layer is deposited on the insulating dielectric layer; and wherein the photocatalyst layer is in face of the plasma.

According to another embodiment of the presently claimed invention, the photocatalyst layer is located within the plasma zone between the at least two spaced plasma electrodes.

According to yet another embodiment of the presently claimed invention, the photocatalyst layer is located at the air inlet of the plasma reactor, or the air outlet of the plasma reactor. At least one surface of the photocatalyst layer is exposed to the plasma zone and in contact with the plasma.

A second aspect of the presently claimed invention is to provide an air purification apparatus.

According to an embodiment of the presently claimed invention, an air purification apparatus comprises: the plasma reactor of the present invention; a casing; an electric fan; a filter; and an orientation air deflector.

A third aspect of the presently claimed invention is to provide an air purification system.

According to an embodiment of the presently claimed invention, an air purification system comprises a plurality of the plasma reactors of the present invention. The plurality of the plasma reactors are in a honeycomb shape and are stacked together.

This plasma driven catalyst air purification apparatus is able to be operated in the ambient conditions, i.e. room temperature, atmospheric pressure and relative humidity. The removable gaseous pollutants include but are not limited to NOx, $SO_2$, $H_2S$, formaldehyde, $NH_3$, volatile organic compounds (VOCs), organic odors, and airborne bacteria and virus. The combination of DBD plasma and $TiO_2$ based catalyst can not only have synergic effect on the disinfection and purification of air but also have low toxic by-products emission. Consequently, the new plasma technology in the present invention, which combines plasma with catalyst, can minimize or even eliminate those drawbacks of the existing plasma technology.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, a plurality of air purification apparatuses and systems are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

The plasma driven catalyst disinfecting and purifying apparatus in this invention can remove air pollutants and improve indoor air quality effectively and efficiently. This apparatus comprises a pre-filter, an electric fan, and a plasma reactor with catalyst inside. The plasma reactor is based on dielectric barrier discharge (DBD) plasma, which comprises two parallel spaced electrodes, and one or two dielectric barriers. The electrode is made of electrically conductive materials which may be in form of rods, tubes, pipe, foils, films, plates, or mesh. The distance between the two electrodes ranges from a few millimeters to one hundred millimeter. The electrodes are separated by the dielectric barriers and these barriers are either attached to the electrodes or inserted between two electrodes. A high voltage alternating current (AC) from 4 kV to 30 kV with the frequency ranging from several hundred hertz (Hz) to a few hundred kilo hertz (kHz) is applied on the electrodes to generate the DBD plasma inside the reactor.

The combination of plasma and catalyst for air treatment has many advantages, such as higher energy efficiencies, low power consumption, high mineralization rates and absence of by-product formation. This plasma driven catalytic air cleaning technology enables deep purification by decomposing a whole range of toxic compositions into $CO_2$ and $H_2O$ at low temperature. Changing plasma characteristics can eventually result in enhancing the production of new active species and increasing the oxidizing power of the plasma discharge. Plasma discharges also affect catalyst properties such as a change in chemical composition, enhancement in surface area, or change of catalytic structure. The catalyst in the plasma zone is activated by the plasma and the activation mechanisms include ozone, UV, local heating, changes in work function, activation of lattice oxygen, adsorption/desorption, creation of electron-hole pairs, and direct interaction of gas-phase radicals with adsorbed pollutants. Besides assisting to degrade the gas pollutants in the plasma reactor, the activated catalyst can also degrade the toxic by-products generated from the plasma. Thus, this plasma driven catalyst technology has much higher air purification efficiency and lower toxic by-products emission than using plasma only, or other air purification technologies.

Figure 1:
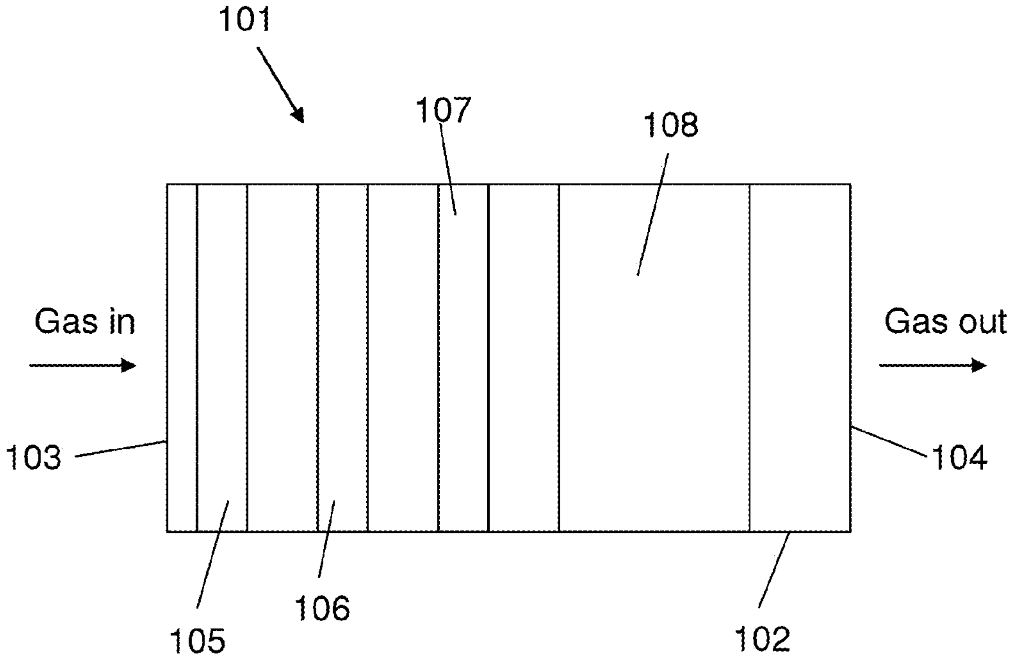
FIG. 1 is a schematic diagram showing a plasma driven catalyst disinfecting and purifying apparatus according to an embodiment of the presently claimed invention.

FIG. 1 is a schematic diagram showing a plasma driven catalyst disinfecting and purifying apparatus according to an embodiment of the presently claimed invention. The apparatus 101 comprises a casing 102 having an air inlet 103, and an air outlet 104, an electric fan 105, an orientation air deflector 106, a pre-filter 107, and a plasma reactor 108. The casing 102 encloses the electric fan 105, the orientation air deflector 106, the filter 107, and the plasma reactor 108. The electric fan 105 generates airflow. The orientation air deflector 106 orientates the direction of the airflow. The pre-filter 107 removes air particulates. The plasma reactor 108 generates plasma for disinfecting and purifying air.

Figure 2:
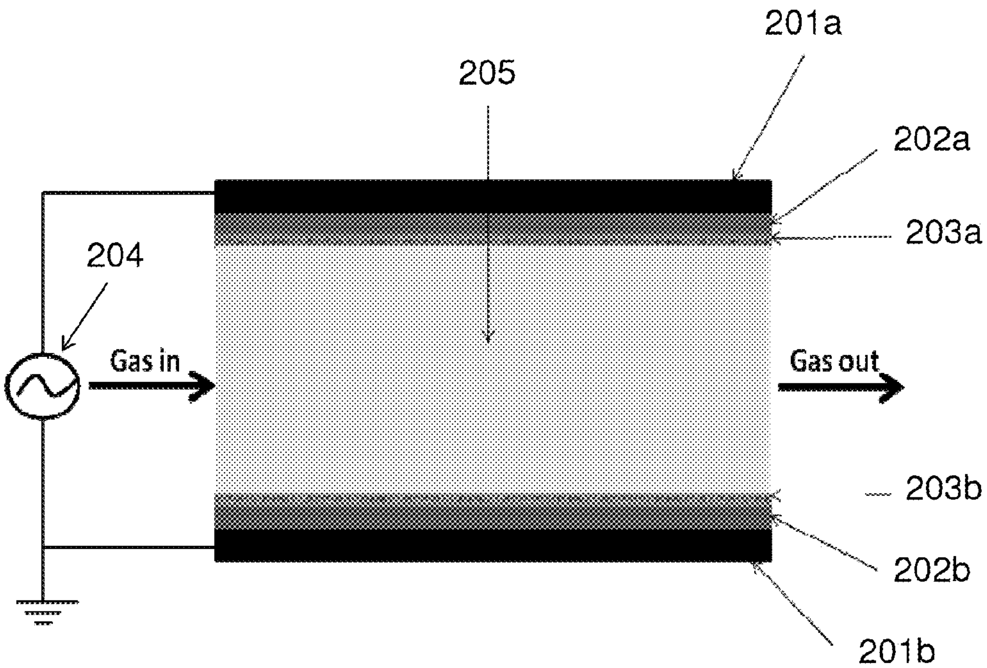
FIG. 2 is a schematic diagram showing a plasma reactor in a PDC apparatus with catalyst coated on electrodes according to an embodiment of the presently claimed invention.

FIG. 2 is a schematic diagram showing a plasma reactor in a PDC apparatus with catalyst coated on electrodes according to an embodiment of the presently claimed invention. The plasma reactor comprises a pair of spaced plasma electrodes, 201*a* and 201*b*, two insulating dielectric layers 202*a* and 202*b*, two photocatalyst layers, 203*a* and 203*b*, an AC power supply 204, an air inlet for gas in and an air outlet for gas out. The spaced plasma electrodes 201*a* and 201*b* are positioned in parallel with each others with a distance. The insulting dielectric layer 202*a* is positioned on the spaced plasma electrode 201*a* and in face of the spaced plasma electrode 201*b*. Similarly, the insulting dielectric layer 202*b* is positioned on the spaced plasma electrode 201*b* and in face of the spaced plasma electrode 201*a*. The photocatalyst layer 203*a* is coated on the insulting dielectric layer 202*a*, and the photocatalyst layer 203*b* is coated on the insulting dielectric layer 202*b*. Such that the photocatalyst layer 203*a* is in face of the spaced plasma electrode 201*b* while the photocatalyst layer 203*b* is in face of the spaced plasma electrode 201*a*. When the AC power supply 204 provides high voltage alternating current to the spaced plasma electrodes 201*a* and 201*b*, a plasma 205 is generated within a plasma zone located between the spaced plasma electrodes 201*a* and 201*b*. Both of the photocatalyst layers 203*a* and 203*b* are in contact with the plasma 205. When polluted air from the air inlet passes through the plasma 205 in the plasma reactor, the polluted air is purified and disinfected, and the purified air is released out from the air outlet.

Since the photocatalyst layers are directly coated on the insulting dielectric layers, the photocatalyst layers can be effectively activated by the plasma in the plasma reactor without additional UV light irradiation to generate free radicals, which enable to decompose air pollutants such as VOC into non-harmful products like water and carbon dioxide, thereby further enhancing the air pollutant removal efficiency. Since the photocatalyst is in contact with the plasma, the efficiency of free radical generation is further increased under such reactive plasma environment. In addition, ozone or other harmful byproducts generated from the plasma are also eliminated by the free radicals.

As the photocatalyst layers are coated on the insulating layers, nearly no air resistance is generated from the photocatalyst layers, ultimately sustaining high airflow condition and reducing the burden of the electric fan of the air purification apparatus.

Figure 3:
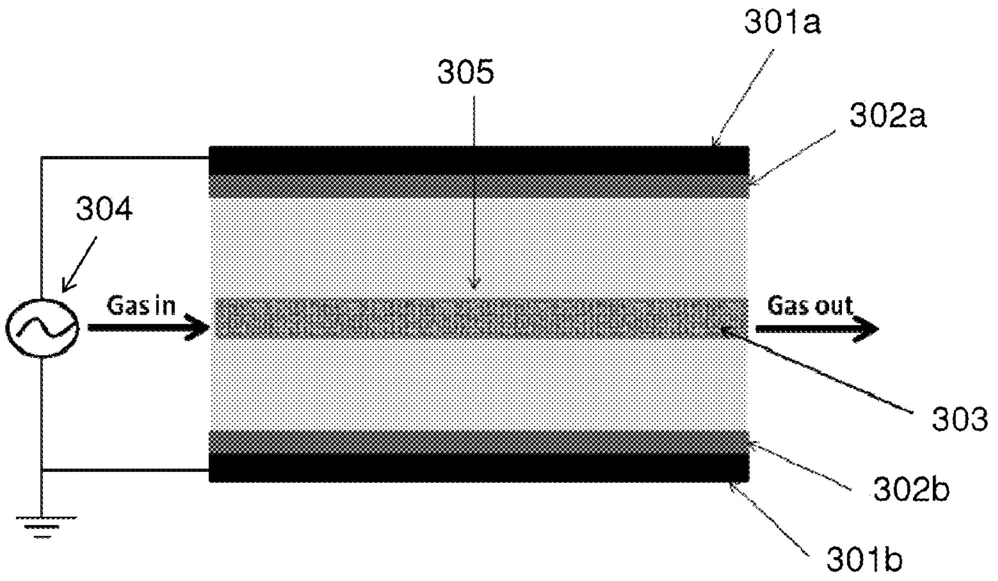
FIG. 3 is a schematic diagram showing a plasma reactor in a PDC apparatus with catalyst located between two electrodes according to an embodiment of the presently claimed invention.

FIG. 3 is a schematic diagram showing a plasma reactor in a PDC apparatus with catalyst located between two electrodes according to an embodiment of the presently claimed invention. In this embodiment, a photocatalyst layer 303 is located in a plasma zone between a pair of plasma spaced electrodes, 301*a* and 301*b*, and placed in substantially parallel with the pair of plasma spaced electrodes, 301*a* and 301*b*. The photocatalyst layer 303 is immersed and in contact with a plasma 305 generated by the pair of the plasma spaced electrodes such that the photocatalyst layer 303 is effectively activated by the plasma 305 to generate free radicals for decomposing air pollutants and eliminating ozone and other harmful by-products released from the plasma 305 without additional UV light irradiation. In addition, as the photocatalyst layer 303 is positioned in parallel along with the airflow, nearly no air resistance is generated from the photocatalyst layer 303. Similarly, insulating dielectric layers 302*a* and 302*b* are coated on the pair of plasma spaced electrodes, 301*a* and 301*b* respectively. An AC voltage is provided to the electrodes by an AC power supply 304 connected to the electrodes.

Preferably, the photocatalyst layer has a thickness ranging of from 10 μm to 500 μm. The insulating dielectric layer has a thickness ranging of 1 mm to 5 mm.

Figure 4:
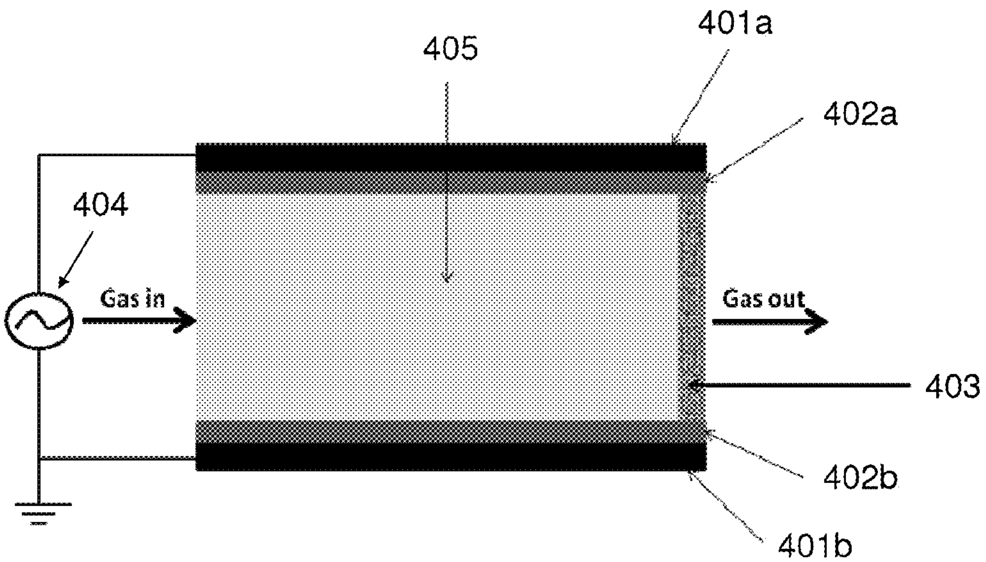
FIG. 4 is a schematic diagram showing a plasma reactor in a PDC apparatus with catalyst located at back end of the plasma reactor according to an embodiment of the presently claimed invention.

FIG. 4 is a schematic diagram showing a plasma reactor with catalyst located at back end of the plasma reactor according to an embodiment of the presently claimed invention. In this embodiment, a photocatalyst layer 403 is located at the back end of the plasma reactor, and covers the air outlet of the plasma reactor. The surface of the photocatalyst layer 403 is exposed to a plasma zone between a pair of plasma spaced electrodes, 401*a* and 401*b*, and in contact with a plasma 405 such that the photocatalyst layer 403 is effectively activated by the plasma 405 to generate free radicals for decomposing air pollutants and eliminating ozone and other harmful by-products released from the plasma 405 without additional UV light irradiation. Such configuration can provide better air pollutant removal efficiency. Similarly, insulating dielectric layers 402*a* and 402*b* are coated on the pair of plasma spaced electrodes, 401*a* and 401*b* respectively. An AC voltage is provided to the electrodes by an AC power supply 404 connected to the electrodes.

Preferably, a $TiO_2$-based coating is incorporated in the reactor. This catalyst has a plurality of mesoporous structures with a pore size of 2-20 nm with the increased total effective surface area. The $TiO_2$ catalyst may be doped with other elements, such as Ti, Zn, Cu, Mn, La, Mo, W, V, Se, Ba, Ce, Sn, Fe, Mg, Au, Pt, Co, Ni, or Pd, or its oxides to enhance its photocatalytic performance. This catalyst can be coated on the dielectric barriers or other substrates, such as air permeable substrate, metal, glass, ceramic, plastic, and fabric. The position of the catalyst can be on the surface of the electrodes, between electrodes, or at the back end or front end of the plasma reactor.

Preferably, the sol-gel method is used to coat the catalyst on the dielectric layer. The precursor of the photocatalyst with other chemicals is mixed well to form a pre-photocatalyst solution. Then the coating is formed on the dielectric layer by dip coating. After that, the coating is annealed in a furnace to form the photocatalyst layer.

Figure 5:
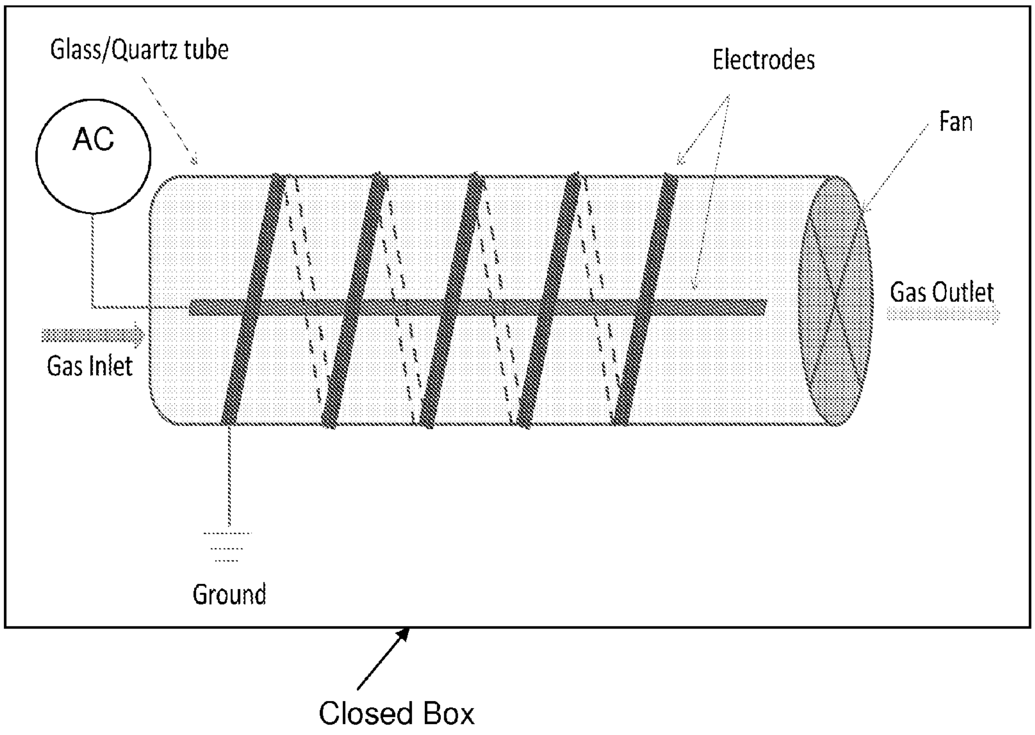
FIG. 5 is a schematic diagram showing an experimental set-up for an air pollutant removal test according to an embodiment of the presently claimed invention.

An experiment was conducted to study the air pollutant removal efficiency with a tubular plasma reactor of the present invention. As shown in FIG. 5, the plasma reactor comprised a dielectric tube with an internal diameter of 14 mm, serving as a dielectric insulating layer. $TiO_2$ was coated on the inner surface of the dielectric tube. A wire was coiled on the outer surface of the dielectric tube as a grounding electrode, and another wire was positioned at the center of the dielectric tube as a high voltage electrode. Both of the electrodes were connected with an AC power supply for providing alternating current towards the electrodes. The plasma reactor was placed in a closed box, in which there was an electric fan for generating airflow. VOC solution was then injected into the closed box, and the concentration of the VOC in the closed box was monitored by a VOC monitor. When an initial VOC concentration reached to a maximum value, the plasma reactor was switched on to generate plasma for purifying air in the closed box. After 30 min, a final VOC concentration was measured to calculate the air pollutant removal efficiency. The tests were repeated with three different AC voltages. A control experiment was conducted by a plasma generator without $TiO_2$ coating, which served as a conventional air purifier with plasma technology only.

Table 1 shows the test results conducted by the plasma reactor of the present invention.

TABLE 1

| Voltage (kV) | Freq. (kHz) | Time (min) | Initial VOC (ppm) | Final VOC (ppm) | Efficiency (%) |
|---|---|---|---|---|---|
| 18 | 6 | 30 | 28 | 15 | 46% |
| 15.2 | 6 | 30 | 27 | 19 | 30% |
| 12 | 6 | 30 | 28 | 23.5 | 16% |

Table 2 shows the test results of the control experiment.

TABLE 2

| Voltage (kV) | Freq. (kHz) | Time (min) | Initial VOC (ppm) | Final VOC (ppm) | Efficiency (%) |
|---|---|---|---|---|---|
| 18 | 6 | 30 | 27 | 18 | 33% |
| 15.2 | 6 | 30 | 27.5 | 22.5 | 18% |
| 12 | 6 | 30 | 28.5 | 26 | 9% |

As shown from the results, the plasma generator of the present invention provides much higher air pollutant removal efficiencies under the three voltages than those of the control experiment. After incorporating the photocatalyst layer on the insulating dielectric layer, the removal efficiencies are substantially increased in a range of 39% to 78%.

An ozone removal test was conducted with the above setup. Ozone monitor was used to measure ozone concentration in the closed box. Two experiments were conducted with the plasma reactor of the present invention (with photocatalyst coating), and a plasma reactor without photocatalyst coating (control experiment) respectively. Initial ozone concentration was measured before switching on the plasma reactor, and final ozone concentration was measured after 30 min. The results are shown in Table 3.

TABLE 3

| | Voltage (kV) | Freq. (kHz) | Time (min) | Initial $O_3$ (ppb) | Final $O_3$ (ppb) |
|---|---|---|---|---|---|
| Without photocatalyst coating | 12 | 6 | 30 | 3 | 362 |
| With photocatalyst coating | 12 | 6 | 30 | 5 | 5 |

As shown from the results, when there was no photocatalyst coating, the ozone concentration substantially increased from 3 ppb to 362 ppb after 30 min. In stark contrast, the ozone concentration remained the same with 5 ppb after 30 min. The results show that the plasma reactor of the present invention is capable of avoiding the release of harmful products generated by the plasma since the photocatalyst is able to remove the harmful products by generation of free radicals.

After the PDC apparatus of the present invention is assembled, the purifier can be put at a predetermined place for disinfecting and purifying indoor air.

If a higher airflow rate is needed, multiple plasma reactors can be integrated together as a honeycomb configuration to form an air purification system. This system can provide higher air purification efficiency, larger airflow rate and longer catalyst lifetime.

Figure 6:
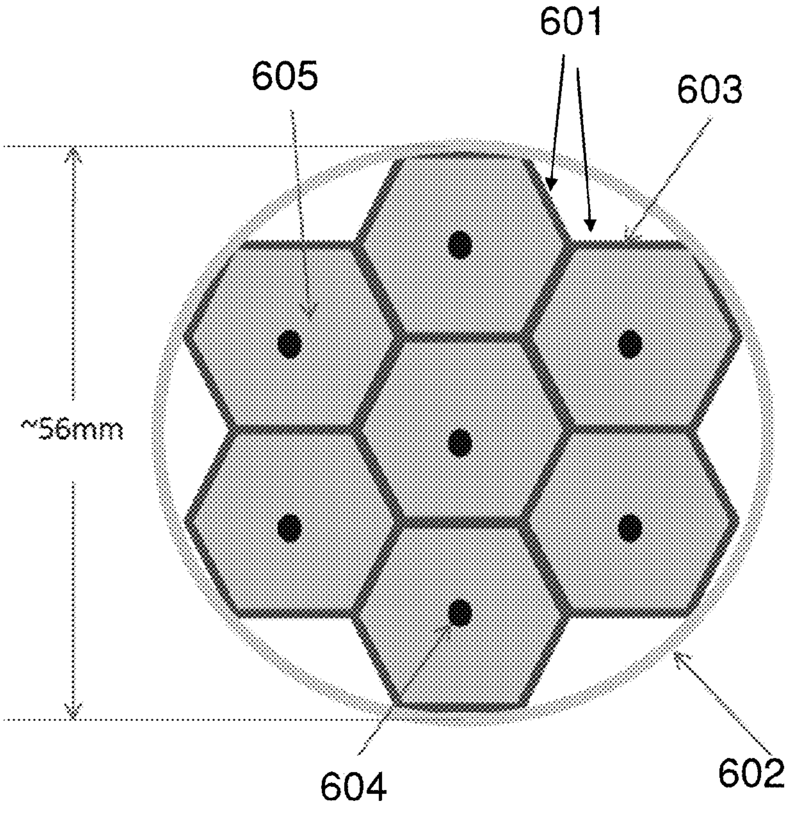
FIG. 6 is a schematic diagram showing a top view of an air purification system with a honeycomb configuration according to an embodiment of the presently claimed invention.

FIG. 6 is a schematic diagram showing a top view of a purification system with a honeycomb configuration according to an embodiment of the presently claimed invention. The system comprises a plurality of plasma reactors 601 of present invention, and a polyethylene terephthalate (PET) plastic shield housing 602. The PET plastic shield housing 602 is 56 mm in diameter and 10 cm in height, and the thickness of the housing 602 is 2-3 mm. Each of the plasma reactors is in a honeycomb shape so that the plasma reactors can be tightly stacked together for space saving. The plasma reactor comprises stainless steel walls 603 having a thickness of 1-2 mm serving as a grounding electrode, and a high voltage electrode 604. There are $TiO_2$ coating and dielectric coating formed on the inner side of the stainless steel walls 603. When an AC power is applied, a plasma 605 is generated between the grounding electrode 603 and the high voltage electrode 604. Since the total plasma zone is substantially increased under such configuration, it is more effective for the air purification system to remove air pollutants.

The present invention is applicable for indoor air quality improvement in domestic and industrial air treatment environment, such as city hall and buildings, airports and train stations, public smoking rooms, underground malls, health care centers, clean manufacturing sites, etc.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. A plasma reactor for purifying air, comprising:

at least two spaced plasma electrodes for generating plasma within a plasma zone between the at least two spaced plasma electrodes by an alternating current voltage;

at least one insulating dielectric layer;

at least one photocatalyst layer; and at least one air inlet and at least one air outlet for allowing air passing through the plasma;

wherein the insulating dielectric layer is formed on at least one of the spaced plasma electrodes;

wherein the photocatalyst layer is deposited on the insulating dielectric layer; and wherein the photocatalyst layer is in face of the plasma.

2. The plasma reactor of claim 1, wherein the photocatalyst layer is in contact with the plasma.

3. The plasma reactor of claim 1, further comprising:

an alternating current power supply connecting to the at least two electrodes for providing the alternating current voltage, wherein the alternating current power supply provides a frequency ranging of 0.1 to 40 kilohertz and the alternating current voltage ranging of 4 to 30 kilovoltz.

4. The plasma reactor of claim 1, wherein at least one of the spaced plasma electrodes comprises a metal, or an electrically-conductive nonmetal, and is in a form of a rod, a tube, a pipe, a foil, a film, a plate, or a mesh.

5. The plasma reactor of claim 1, wherein the at least two spaced plasma electrodes are placed in parallel with each other with a distance of 1 mm to 100 mm.

6. The plasma reactor of claim 1, wherein the insulating dielectric layer comprises ceramic, quartz, or glass.

7. The plasma reactor of claim 1, wherein the photocatalyst layer comprises titantium dioxide, which further comprises one or more of Ti, Zn, Cu, Mn, La, Mo, W, V, Se, Ba, Ce, Sn, Fe, Mg, Au, Pt, Co, Ni, Pd, their oxides thereof, or their alloys thereof.

8. An air purification apparatus, comprising the plasma reactor of claim 1.

9. The air purification apparatus of claim 8, further comprising:

a casing;

an electric fan;

a filter; and an orientation air deflector.

10. An air purification system, comprising a plurality of the plasma reactors of claim 1.

11. The air purification system of claim 10, wherein the plurality of the plasma reactors are in a honeycomb shape and stacked together.

12. A plasma reactor for purifying air, comprising:

at least two spaced plasma electrodes for generating plasma within a plasma zone between the at least two spaced plasma electrodes by an alternating current voltage;

at least one insulating dielectric layer;

at least one photocatalyst layer; and at least one air inlet and at least one air outlet for allowing air passing through the plasma;

wherein the insulating dielectric layer is formed on at least one of the spaced plasma electrodes; and wherein the photocatalyst layer is located within the plasma zone between the at least two spaced plasma electrodes.

13. The plasma reactor of claim 12, wherein the photocatalyst layer is coated on an air permeable substrate, glass, ceramic, plastic or fabric.

14. The plasma reactor of claim 12, wherein the photocatalyst layer comprises titantium dioxide, which further comprises one or more of Ti, Zn, Cu, Mn, La, Mo, W, V, Se, Ba, Ce, Sn, Fe, Mg, Au, Pt, Co, Ni, Pd, their oxides thereof, or their alloys thereof.

15. The plasma reactor of claim 12, further comprising:

an alternating current power supply connecting to the at least two electrodes for providing the alternating current voltage, wherein the alternating current power supply provides a frequency ranging of 0.1 to 40 kilohertz and the alternating voltage ranging of 4 to 30 kilovoltz.

16. An air purification apparatus, comprising the plasma reactor of claim 12.

17. The air purification apparatus of claim 16, further comprising:

a casing;

an electric fan;

a filter; and an orientation air deflector.

18. An air purification system, comprising a plurality of the plasma reactors of claim 12.

19. The air purification system of claim 18, wherein the plurality of the plasma reactors are in a honeycomb shape and stacked together.

20. A plasma reactor for purifying air, comprising:

at least two spaced plasma electrodes for generating plasma within a plasma zone between the at least two spaced plasma electrodes by an alternating current voltage;

at least one insulating dielectric layer;

at least one photocatalyst layer; and at least one air inlet and at least one air outlet for allowing air passing through the plasma;

wherein the insulating dielectric layer is formed on at least one of the spaced plasma electrodes;

wherein the photocatalyst layer is located at the air inlet or the air outlet; and wherein at least one surface of the photocatalyst layer is exposed to the plasma zone and in contact with the plasma.

* * * * *